(12) United States Patent
Milanole et al.

(10) Patent No.: US 11,578,031 B2
(45) Date of Patent: Feb. 14, 2023

(54) DISSYMMETRIC N,N-DIALKYLAMIDES USED PARTICULARLY FOR SEPARATING URANIUM(VI) FROM PLUTONIUM(IV), SYNTHESIS THEREOF AND USES OF SAME

(71) Applicants: COMMISSARIAT À L'ÉNERGIE ATOMIQUE ET AUX ÉNERGIES ALTERNATIVES, Paris (FR); Orano Cycle, Courbevoie (FR); ELECTRICITE DE FRANCE, Paris (FR)

(72) Inventors: Gaëlle Milanole, Orange (FR); Emilie Russello, Bagnol sur Ceze (FR); Cécile Marie, Avignon (FR); Manuel Miguirditchian, Avignon (FR); Christian Sorel, Villeneuve les Avignon (FR)

(73) Assignees: COMMISSARIAT À L'ÉNERGIE ATOMIQUE ET AUX ÉNERGIES ALTERNATIVES, Paris (FR); ORANO RECYCLAGE, Châtillon (FR); ELECTRICITE DE FRANCE, Paris (FR)

( * ) Notice: Subject to any disclaimer, the term of this patent is extended or adjusted under 35 U.S.C. 154(b) by 613 days.

(21) Appl. No.: 16/479,830

(22) PCT Filed: Jan. 25, 2018

(86) PCT No.: PCT/FR2018/050172
§ 371 (c)(1),
(2) Date: Jul. 22, 2019

(87) PCT Pub. No.: WO2018/138441
PCT Pub. Date: Aug. 2, 2018

(65) Prior Publication Data
US 2021/0332002 A1     Oct. 28, 2021

(30) Foreign Application Priority Data
Jan. 26, 2017 (FR) ...................................... 1750657

(51) Int. Cl.
*C07C 233/05*     (2006.01)
*C22B 3/32*     (2006.01)
(Continued)

(52) U.S. Cl.
CPC ............. *C07C 233/05* (2013.01); *C22B 3/32* (2021.05); *C22B 60/026* (2013.01); *C22B 60/04* (2013.01);
(Continued)

(58) Field of Classification Search
CPC ....... C07C 233/05; C07C 231/02; C22B 3/32; C22B 60/026; C22B 60/04; G21C 19/46; Y02P 10/20; Y02E 30/30
(Continued)

(56) References Cited

U.S. PATENT DOCUMENTS

| 4,772,429 A | 9/1988 | Descouls et al. |
| 5,132,092 A | 7/1992 | Musikas et al. |

(Continued)

FOREIGN PATENT DOCUMENTS

| EP | 0228940 A1 | 7/1987 |
| FR | 2465687 A1 * | 9/1979 |

(Continued)

OTHER PUBLICATIONS

STN registry file for the compound having RN: 959055-41-5, Dec. 20, 2007 (Year: 2007).*
(Continued)

*Primary Examiner* — Melissa S Swain
(74) *Attorney, Agent, or Firm* — Pearne & Gordon LLP

(57) ABSTRACT

A dissymmetric RN,N-dialkylamides of formula (I) in which: $R^1$ represents a linear $C_1$ to $C_4$ alkyl, $R^2$ represents a linear $C_1$ to $C_{10}$ alkyl, and $R^3$ represents a linear or branched $C_6$ to $C_{15}$ alkyl, where $R^3$ is different from a n-octyl, n-decyl, n-dodecyl, 2-ethylhexyl and 2-ethyloctyl group when $R^1$ (Continued)

represents a n-butyl group and $R^2$ represents an ethyl group. A method for synthesising the N,N-dialkylamides, and uses of same for extracting uranium and/or plutonium from an aqueous acid solution or for fully or partially separating the uranium from the plutonium contained in an aqueous acid solution and a solution resulting from the dissolution of spent nuclear fuel in nitric acid. A method for treating an aqueous solution resulting from the dissolution of spent nuclear fuel in nitric acid, which allows the uranium and the plutonium contained in the solution to be extracted, separated and decontaminated in a single cycle.

19 Claims, 1 Drawing Sheet

(51) Int. Cl.
  *C22B 60/02* (2006.01)
  *C22B 60/04* (2006.01)
  *G21C 19/46* (2006.01)
  *C07C 231/02* (2006.01)
(52) U.S. Cl.
  CPC ............ *G21C 19/46* (2013.01); *C07C 231/02* (2013.01); *Y02E 30/30* (2013.01); *Y02P 10/20* (2015.11)
(58) Field of Classification Search
  USPC .......................................................... 75/398
  See application file for complete search history.

(56) References Cited

U.S. PATENT DOCUMENTS

| 2013/0202501 A1* | 8/2013 | Saudray .................. C22B 3/065 423/10 |
|---|---|---|
| 2018/0222849 A1 | 8/2018 | Miguirditchian et al. |

FOREIGN PATENT DOCUMENTS

| FR | 2591213 A1 | 12/1985 |
|---|---|---|
| FR | 2642562 A1 | 2/1989 |
| FR | 2642561 A1 | 8/1990 |
| GB | 2183078 A | 5/1987 |

OTHER PUBLICATIONS

Search Report for French Application No. 1750657 dated Oct. 30, 2017.
International Search Report for PCT/FR2018/050172 dated Apr. 26, 2018.
Written Opinion for or PCT/FR2018/050172 dated Apr. 26, 2018.
Prabhu, D.R. et al. Extraction of Uranium (VI) and Plutonium(IV) with Unsymmetrical Monoamides: IN: Radiochimica Acta, 1993, vol. 60, pp. 109-114.
Ruikar, P.B. et al., "Extraction of Uranium, Plutonium And Some Fission Products with y-Irradiated Unsymmetrical And Branched Chain Dialkylamides" In: Journal of Radioanalytical and Nuclear Chemistry, 1993, vol. 176, No. 2, pp. 103-111.
Guoxin, Sun et al. "Extraction of U(VI) with unsymmetrical N-methyl-N-octyl alkylamides in toluene" In: ournal of Radioanalytical and Nuclear Chemistry, 2005, vol. 265, No. 3, pp. 711-713.
Yu, By Cui et al. "Extraction of U9VI) with unsymmetrical N-methyl-N-decylalkylamide in toluene" In: Radiochimica Acta 2005, vol. 93, pp. 287-290.
Mandeville, Simon J. et al. "The influence of the size and structure of a spectator alkyl group on the relative rates of alkyl radical elimination from ionised tertiary amines" In: European journal of mass spectrometry, 1999, vol. 5, pp. 339-351.
Abstract of "The influence of the size and structure of a spectator alkyl group on the relative rates of alkyl radical elimination from ionised tertiary amines" from 1999 European journal of mass spectrometry,CAPLUS, The American Chemical Society; Supplementary Disclosures, retrieved on Sep. 1, 2021.

* cited by examiner

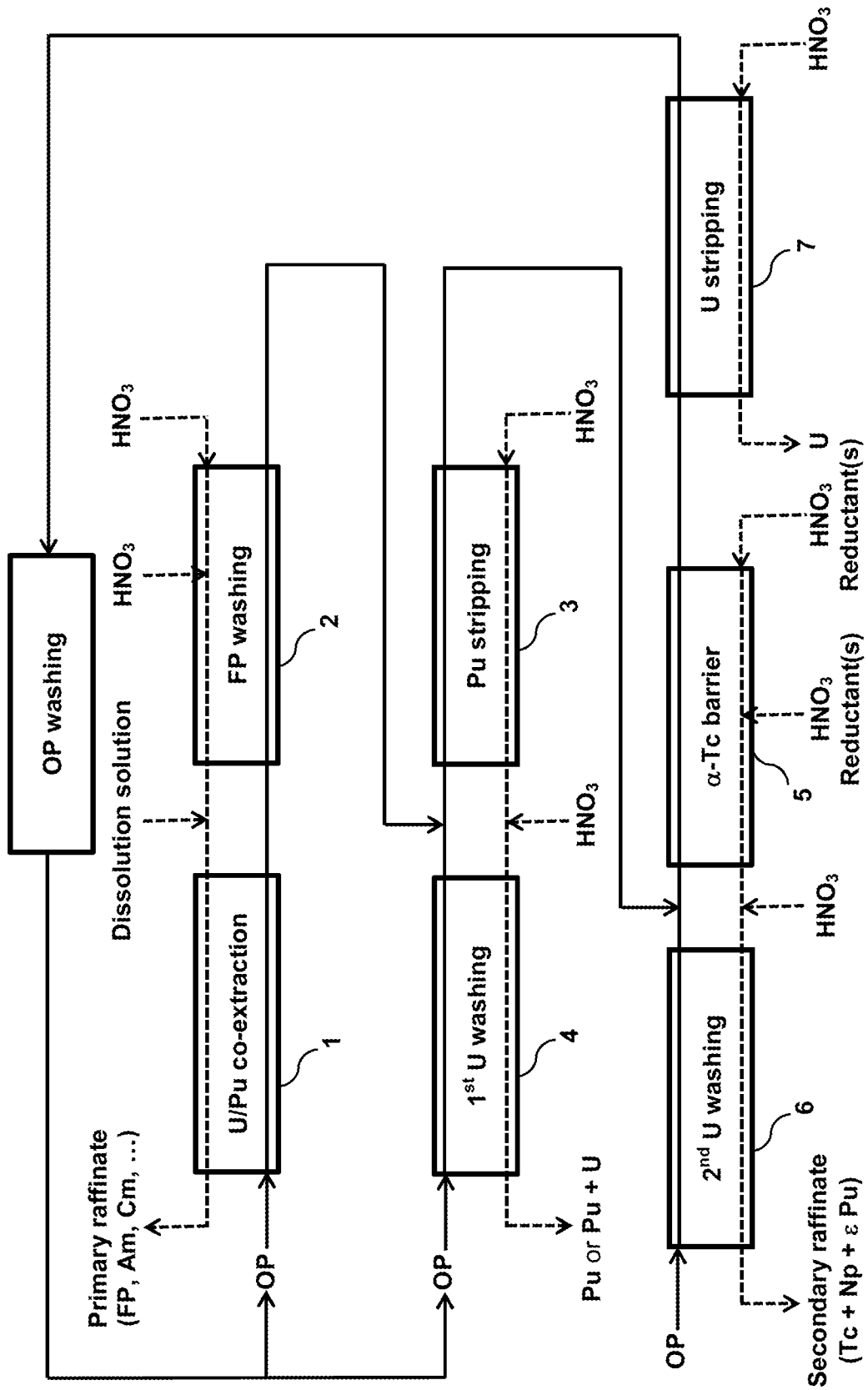

DISSYMMETRIC N,N-DIALKYLAMIDES USED PARTICULARLY FOR SEPARATING URANIUM(VI) FROM PLUTONIUM(IV), SYNTHESIS THEREOF AND USES OF SAME

CROSS-REFERENCE TO RELATED APPLICATIONS

This is a National Stage application of PCT international application PCT/FR2018/050172, filed on Jan. 25, 2018, which claims the priority of French Patent Application No. 17 50657, filed Jan. 26, 2017, both of which are incorporated herein by reference in their entireties.

TECHNICAL FIELD

The invention relates to novel dissymmetric N,N-dialkylamides and to a method allowing the synthesis thereof.

It also relates to the use of these N,N-dialkylamides, as extractants, to extract uranium(VI) and/or plutonium(IV) from an acid aqueous solution and in particular from an aqueous solution resulting from the dissolution of a spent nuclear fuel in nitric acid.

It further relates to the use of these N,N-dialkylamides, as extractants, to separate totally or partially uranium(VI) from plutonium(IV) from an acid aqueous solution and in particular from an aqueous solution resulting from the dissolution of a spent nuclear fuel in nitric acid.

It further relates to a method for processing an aqueous solution resulting from the dissolution of a spent nuclear fuel in nitric acid, allowing the uranium(VI) and plutonium (IV) contained in this solution to be extracted, separated and decontaminated in a single cycle without having recourse to any reduction operation of plutonium(IV), and wherein one of these N,N-dialkylamides or a mixture thereof is used as extractant.

The invention finds particular application in the processing of spent nuclear fuels containing uranium (notably uranium oxides—UOXs) or containing both uranium and plutonium (notably mixed oxides of uranium and plutonium—MOXs).

STATE OF THE ART

The PUREX process, that is implemented in all spent nuclear fuel processing plants existing world-wide (La Hague in France, Rokkasho in Japan, Sellafield in the United Kingdom, etc.), uses tri-n-butyl phosphate (or TBP) as extractant to recover uranium and plutonium via liquid-liquid extraction from aqueous solutions resulting from the dissolution of these fuels in nitric acid.

In this process, TBP is used in a 30% (v/v) solution in an organic diluent (hydrogenated tetrapropylene (TPH) or n-dodecane). This organic solution is commonly called a «solvent» in the field under consideration.

The recovery of uranium and plutonium with the PUREX process is conducted in several cycles:
- a first purification cycle of uranium and plutonium (called «1CUPu»), intended to decontaminate the uranium and plutonium with respect to americium, curium and fission products, with a partitioning of uranium and plutonium into two aqueous streams in this first cycle via a reductive stripping of plutonium;
- a second purification cycle of uranium (called «2CU»), intended to complete the decontamination of uranium to reach the specifications defined by ASTM standards for uranium as end product; and
- a second cycle, and in some plants a third purification cycle of plutonium (respectively called «2CPu» and «3CPu»), intended to complete the decontamination of plutonium to reach the specifications defined by ASTM standards for plutonium as end product, and for concentration thereof before conversion to oxide.

The performance afforded by the PUREX process is satisfactory and the feedback of experience acquired since the start-up of the plants applying this process is positive.

However, the use of TBP has limitations preventing the possibility to reach with this extractant the objectives of simplicity, compactness and improved safety that have been set for the future processing plants of spent nuclear fuels, which notably target the partitioning of uranium and plutonium into two aqueous streams without the use of reducing agents.

These limitations are the following:
- the uranium and plutonium decontamination factors with respect to some fission products (technetium and ruthenium) and transuranium elements (Np) are insufficient at the end of the first purification cycle, hence the impossibility of achieving with TBP a scheme which would lead in a single cycle to end products meeting the aforementioned specifications;
- the partitioning of uranium and plutonium into two aqueous streams requires the reducing of plutonium(IV) to plutonium(III) (since, with TBP, the separation factor between uranium(VI) and plutonium(IV) is insufficient irrespective of the acidity of the aqueous solution used to obtain this partitioning) and therefore requires the use of reducing and anti-nitrous agents in large amounts which, via degradation, generate unstable, reactive species that are therefore restrictive in terms of safety;
- the degradation products of TBP impact the performance of the process; in particular, di-n-butyl phosphate (or DBP) leads to the formation of metal complexes of which some are insoluble and can cause retaining of plutonium in the solvent, hence the need to carry out an operation known as «Pu barrier» which is downstream of the plutonium reductive stripping and which is intended to complete this stripping;
- the risk of formation of a $3^{rd}$ phase induced by the presence of plutonium limits the implementation of a plutonium concentrating scheme (for criticality risks) or of a scheme allowing the processing of spent nuclear fuels with high plutonium content such as MOX fuels issued from light water reactors or fast neutron reactors;
- the stripping of uranium from the solvent in which it was previously extracted is incomplete if conducted at ambient temperature, hence the need to perform this stripping at a temperature of 50° C. (corresponding to the maximum temperature allowed by the flash point of the solvent); however, even at this temperature, the stripping of uranium is non-concentrating (the ratio of organic/aqueous flows (O/A) being 1 or less 1);
- the solubility of TBP, which is non-negligible in aqueous phase (up to 300 mg/L depending on the acidity of the aqueous phase), necessitates washes with organic diluent of the aqueous phases resulting from the different extraction cycles to recover the TBP solubilized in these aqueous phases; and
- the incineration of TBP and of its degradation products generates secondary waste including solid phosphate-containing residues.

Therefore, with the prospect of future nuclear fuel processing plants that are simpler and more compact than current plants and having further improved safety, the inventors set themselves the objective of developing a method which, whilst giving just as good performance as the PUREX process in terms of recovery and decontamination of uranium and plutonium contained in aqueous nitric solutions resulting from the dissolution of spent nuclear fuels, allows overcoming all the limitations related to the use as TBP as extractant, and in particular only comprises a single processing cycle and is free of any operation for reductive stripping of plutonium.

The Inventors therefore first focused on finding extractants having the required properties to make the development of said method possible.

N,N-dialkylamides happen to represent a family of extractants that has been largely researched as a possible alternative to TBP for the processing of spent nuclear fuels, in particular because they generally have good affinity for uranium and plutonium under strong acidity, are less soluble than TBP in aqueous phase, are fully incinerable (CHON system) and have degradation products that are less problematic than those of TBP.

There are two types of N,N-dialkylamides:
so-called «symmetric» N,N-dialkylamides since the two alkyl groups carried by the nitrogen atom are identical; and
and so-called «dissymmetric» N,N-dialkylamides since the two alkyl groups carried by the nitrogen atom are different.

Symmetric N,N-dialkylamides were the first to be researched. For example, three patent applications (FR-A-2 591 213, FR-A-2 642 561 and FR-A-2 642 562, hereafter references [1], [2] and [3]), relating to the use of symmetric N,N-dialkylamides as extractants for the processing of spent nuclear fuels, were filed in the 1980s, two of which, namely references [1] and [3], envisage the possibility of partitioning uranium and plutonium with these N,N-dialkylamides without carrying out a reductive stripping operation of plutonium.

Some of the symmetric N,N-dialkylamides proposed in references [1] and [3] effectively allow co-extracting uranium(VI) and plutonium(IV) from a highly acid aqueous solution, followed by separating thereof under lower acidity without having to reduce the plutonium.

However, these N,N-dialkylamides prove to obtain lesser extraction of plutonium than TBP from a highly acid aqueous phase. As a result, to obtain a quantitative extraction of plutonium, the number of extraction stages needs to be increased compared with the number required for TBP, which goes against the targeted objective of compactness.

Thereafter dissymmetric N,N-dialkylamides gave rise to a certain number of studies among which mention can be made of those conducted by the Bhabha Atomic Research Centre in Bombay (see, for example, the publications by Ruikar et al., *Journal of Radioanalytical and Nuclear Chemistry* 1993, 176(2), 103-111, and Prabhu et al., *Radiochimica Acta* 1993, 60, 109-114, hereafter references [4] and [5]) and those conducted by the group led by Guo-Xin Sun at Jinan University (see, for example, the publications by Cui et al., *Radiochimica Acta* 2005, 93, 287-290, and by Sun et al., *Journal of Radioanalytical and Nuclear Chemistry* 2005, 264(3), 711-713, hereafter references [6] and [7]).

However, aside from the fact that the results of these studies are fragmented and sometimes contradictory, none thereof suggest the possibility of separating uranium from plutonium without reducing the latter.

SUMMARY OF THE INVENTION

The first subject of the invention is therefore an N,N-dialkylamide of formula (I) below:

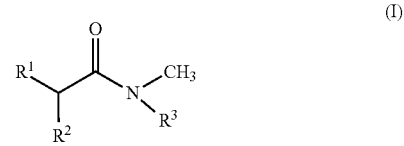

wherein:
$R^1$ is a linear alkyl group having 1 to 4 carbon atoms;
$R^2$ is a linear alkyl group having 1 to 10 carbon atoms;
$R^3$ is a linear or branched alkyl group having 6 to 15 carbon atoms;
provided that $R^3$ differs from an n-octyl, n-decyl, n-dodecyl, 2-ethylhexyl and 2-ethyloctyl group when $R^1$ is a n-butyl group and $R^2$ is an ethyl group.

In the foregoing and in the remainder hereof, the expressions «from ... to ...», «ranging from ... to ...» and «of between ... and ...» are equivalent and are meant to indicate that the limits are included.

Therefore by «linear alkyl group having 1 to 4 carbon atoms», it is meant an alkyl group selected from among the methyl, ethyl, n-propyl and n-butyl groups.

By «linear alkyl group having 1 to 10 carbon atoms», it is meant any alkyl group selected from among the methyl, ethyl, n-propyl, n-butyl, n-pentyl, n-hexyl, n-heptyl, n-octyl, n-nonyl and n-decyl groups, whilst by «linear or branched alkyl group having 6 to 15 carbon atoms», it is meant any alkyl group having 6, 7, 8, 9, 10, 11, 12, 13, 14 or 15 carbon atoms and having zero, one or several same or different branches such as an n-pentyl, n-hexyl, n-heptyl, n-octyl, n-nonyl, n-decyl, n-undecyl, n-dodecyl, n-tridecyl or n-tetradecyl group substituted by a methyl group (e.g. a 2- or 4-methylpentyl group, 2- or 4-methylhexyl group, 2- or 4-methylheptyl group, etc.); an n-butyl, n-pentyl, n-hexyl, n-heptyl, n-octyl, n-nonyl, n-decyl, n-undecyl, n-dodecyl or n-tridecyl group substituted by an ethyl group (e.g. a 2-ethylbutyl, 2-ethylpentyl group, 2- or 4-ethylhexyl group, a 2- or 4 ethyloctyl group, a 2- or 4-ethyldecyl group, etc.); an n-butyl, n-pentyl, n-hexyl, n-heptyl, n-octyl, n-nonyl, n-decyl, n-undecyl or n-dodecyl group substituted by an n-propyl or isopropyl group; an n-pentyl, n-hexyl, n-heptyl, n-octyl, n-nonyl, n-decyl or n-undecyl group substituted by an n-butyl, iso-butyl, sec-butyl or Cert-butyl group; an n-butyl, n-pentyl, n-hexyl, n-heptyl, n-octyl, n-nonyl, n-decyl, n-undecyl, n-decyl or n-tridecyl group substituted by two methyl groups; an n-butyl, n-pentyl, n-hexyl, n-heptyl, n-octyl, n-nonyl, n-decyl, n-undecyl or n-dodecyl group substituted by a methyl group and by an ethyl group (e.g. 3-ethyl-4-methylhexyl group, 3-methyl-4-ethylhexyl group, 3-ethyl-4-methyloctyl group, 3-methyl-4-ethyloctyl group); etc.

Also, the expressions «aqueous solution» and «aqueous phase» are equivalent and interchangeable, as are the expressions «organic solution» and «organic phase».

According to the invention, it is preferred that:
$R^1$ is a methyl, ethyl or n-propyl group, and/or
$R^2$ is an n-propyl, n-butyl, n-pentyl, n-hexyl or n-heptyl group, and/or
$R^3$ is an n-hexyl, n-heptyl, n-octyl, 2-ethylhexyl, n-nonyl, n-decyl or 2-ethyloctyl group;

again provided that $R^3$ differs from an n-octyl, n-decyl, n-dodecyl, 2-ethylhexyl or 2-ethyloctyl group when $R^1$ is an n-butyl group and $R^2$ is an ethyl group.

In addition, it is preferred that the total number of carbon atoms of the N,N-dialkylamide is 17, 18 or 19.

Advantageously, the N,N-dialkylamide is selected from among:
the N,N-dialkylamide wherein $R^1$ is a methyl group, $R^2$ is an n-butyl group and $R^3$ is an n-nonyl group;
the N,N-dialkylamide wherein $R^1$ and $R^2$ are each an n-propyl group and $R^3$ is an n-octyl group; and
the N,N-dialkylamide wherein $R^1$ is an n-propyl group, $R^2$ is an n-pentyl group and $R^3$ is an n-hexyl group.

The N,N-dialkylamides defined above are advantageously obtained by reacting a carboxylic acid of formula (II) below:

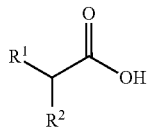

(II)

wherein:
$R^1$ is a linear alkyl group having 1 to 4 carbon atoms;
$R^2$ is a linear alkyl group having 1 to 10 carbon atoms;
with an amine of formula $HN(CH_3)R^3$ wherein $R^3$ is a linear alkyl group having 6 to 15 carbon atoms, in an organic solvent and in the presence of a coupling agent;
provided that $R^3$ differs from an n-octyl, n-decyl, n-dodecyl, 2-ethylhexyl and 2-ethyloctyl group when $R^1$ is an n-butyl group and $R^2$ is an ethyl group.

Therefore, a further subject of the invention is a method for synthesizing N,N-dialkylamides which comprises this reaction.

The coupling agent can be any coupling agent able to be used for peptide synthesis in a liquid medium and in particular a carbodiimide such as 1,3-dicyclohexylcarbodiimide (or DDC) or 1-ethyl-3-(3-dimethylaminopropyl) carbodiimide (or EDC).

This coupling agent is advantageously used jointly with an activator such as a triazole, e.g. 1-hydroxybenzotriazole (or HOBt) or 1-hydroxyazabenzotriazole (or HOAt).

The above-defined N,N-dialkylamides have proved to be capable of extracting uranium(VI) and plutonium(IV) very efficiently from an acid aqueous solution such as an aqueous nitric solution.

Therefore, a further subject of the invention is the use of an N,N-dialkylamide or a mixture of N,N-dialkylamides such as previously defined, to extract uranium(VI) and/or plutonium(IV) from an acid aqueous solution.

According to the invention, uranium and/or plutonium are preferably extracted from the acid aqueous solution by liquid-liquid extraction, i.e. by contacting this aqueous solution with an organic solution comprising the N,N-dialkylamide or the mixture of N,N-dialkylamides in an organic diluent, and then separating the aqueous and organic solutions.

In this case, the organic solution preferably comprises from 1 mol/L to 2 mol/L and better still from 1.1 mol/L to 1.4 mol/L, e.g. 1.2 mol/L, of the N,N-dialkylamide or mixture of N,N-dialkylamides.

The acid aqueous solution is preferably an aqueous solution resulting from the dissolution of a spent nuclear fuel in nitric acid, i.e. an aqueous solution typically comprising from 3 mol/L to 6 mol/L of nitric acid.

In addition to being capable of quantitatively extracting uranium(VI) and plutonium(IV) from an acid aqueous solution, the above-defined N,N-dialkylamides have proved to allow a subsequent separation of the uranium from the plutonium thus extracted without reducing plutonium, this separation possibly being:
either a total separation of uranium from plutonium, i.e. whereby two aqueous solutions are obtained, one containing plutonium without uranium and the other containing uranium without plutonium;
or a partial separation of uranium from plutonium, i.e. whereby two aqueous solutions are obtained, one containing a mixture of plutonium and uranium and the other containing uranium without plutonium.

Therefore, a further subject of the invention is the use of an N,N-dialkylamide or a mixture of N,N-dialkylamides such as previously defined to totally or partially separate uranium(VI) from plutonium(IV) from an acid aqueous solution, which use comprising:

a) a co-extraction of uranium and plutonium from the aqueous solution, this co-extraction comprising at least one contacting of the aqueous solution with an organic solution comprising the N,N-dialkylamide or the mixture of N,N-dialkylamides as extractant, in solution in an organic diluent, followed by a separation of the aqueous and organic solutions;

b) a stripping of plutonium, in oxidation state +IV, from the organic solution resulting from step a), this stripping comprising at least one contacting of the organic solution with an aqueous solution comprising from 0.1 mol/L to 0.5 mol/L of nitric acid, followed by a separation of the organic and aqueous solutions; and c) an extraction of all or part of the uranium fraction contained in the aqueous solution resulting from step b), this extraction comprising at least one contacting of the aqueous solution with an organic solution having the same composition as the organic solution used at step a), followed by a separation of the aqueous and organic solutions;
whereby an aqueous solution is obtained comprising plutonium without uranium, or a mixture of plutonium and uranium, and an organic solution comprising uranium without plutonium.

The organic solution used at step a) and therefore the one used at step c) preferably comprise from 1 mol/L to 2 mol/L, and better still from 1.1 mol/L to 1.4 mol/L, e.g. 1.2 mol/L, of the N,N-dialkylamide or mixture of N,N-dialkylamides.

With regard to the acid aqueous solution from which uranium and plutonium are co-extracted, this is preferably an aqueous solution resulting from the dissolution of a spent nuclear fuel in nitric acid, i.e. an aqueous solution typically comprising from 3 mol/L to 6 mol/L of nitric acid.

The uranium contained in the organic solution resulting from step c) can then be stripped from this phase by contacting the organic solution with an aqueous solution comprising no more than 0.5 mol/L and better still no more than 0.05 mol/L of nitric acid, followed by a separation of the organic and aqueous solutions.

In addition to exhibiting the aforementioned properties, the above-defined N,N-dialkylamides have proved to allow an extraction of uranium(VI) and plutonium(IV) from an aqueous solution resulting from the dissolution of a spent nuclear fuel in nitric acid, with very high separation factors with respect to the main fission products contained in this solution.

Having regard to this accumulation of properties, these N,N-dialkylamides have allowed the development of a method for processing an aqueous nitric solution resulting from the dissolution of a spent nuclear fuel, which whilst giving just as good performance as the PUREX process in terms of recovery and decontamination of the uranium and plutonium contained in said solution, is free of any reductive stripping of plutonium and only comprises a single processing cycle.

Therefore, a further subject of the invention is a single-cycle method for processing an aqueous solution resulting from the dissolution of a spent nuclear fuel in nitric acid, the aqueous solution comprising uranium, plutonium, americium, curium and fission products including technetium, the cycle comprising:

a) a co-extraction of uranium and plutonium from the aqueous solution, the co-extraction comprising at least one contacting, in an extractor, of the aqueous solution with an organic solution comprising an N,N-dialkylamide or a mixture of N,N-dialkylamides as defined above as extractant, in solution in an organic diluent, followed by a separation of the aqueous and organic solutions;

b) a decontamination of the organic solution resulting from step a) with respect to americium, curium and fission products, this decontamination comprising at least one contacting, in an extractor, of the organic solution with an aqueous solution comprising from 1 mol/L to 6 mol/L of nitric acid, followed by a separation of the organic and aqueous solutions;

c) a partitioning of the uranium and plutonium contained in the organic solution resulting from step b) into an aqueous solution comprising either plutonium without uranium, or a mixture of plutonium and uranium, and an organic solution comprising uranium without plutonium, this partitioning comprising:

$c_1$) a stripping of plutonium, in oxidation state +IV, and of a fraction of the uranium from the organic solution resulting from step b), this stripping comprising at least one contacting, in an extractor, of the organic solution with an aqueous solution comprising from 0.1 mol/L to 0.5 mol/L of nitric acid, followed by a separation of the organic and aqueous solutions;

$c_2$) an extraction of all or part of the uranium fraction contained in the aqueous solution resulting from $c_1$), this extraction comprising at least one contacting, in an extractor, of the aqueous solution with an organic solution identical to the organic solution used at step a), followed by a separation of the aqueous and organic solutions;

d) a decontamination of the organic solution resulting from step $c_1$) with respect to technetium, the decontamination comprising:

$d_1$) a stripping of technetium, in oxidation state +IV, from the organic solution resulting from step $c_1$), this stripping comprising at least one contacting, in an extractor, of the organic solution with an aqueous solution comprising from 0.1 mol/L to 3 mol/L of nitric acid and at least one reducing agent capable of reducing technetium from oxidation state +VII to oxidation state +IV, followed by a separation of the organic and aqueous solutions;

$d_2$) an extraction of the uranium fraction contained in the aqueous solution resulting from step $d_1$), this extraction comprising at least one contacting, in an extractor, of the aqueous solution with an organic solution identical to the organic solution used at step a), followed by a separation of the aqueous and organic solutions;

e) a stripping of uranium from the organic solution resulting from $d_1$), this stripping comprising at least one contacting, in an extractor, of the organic solution with an aqueous solution comprising no more than 0.5 mol/L of nitric acid, followed by a separation of the organic and aqueous solutions; and f) a regeneration of the organic phase resulting from step e);

whereby a first and a second aqueous solution are obtained, decontaminated with respect to americium, curium and fission products including technetium, the first aqueous solution comprising plutonium without uranium, or a mixture of plutonium and uranium, and the second aqueous solution comprising uranium without plutonium.

According to the invention, the organic solution used at step a) and hence those used at steps $c_2$) and $d_2$) since the organic solutions used at steps a), $c_2$) and $d_2$) have the same composition, preferably comprise from 1 mol/L to 2 mol/L and better still from 1.1 mol/L to 1.4 mol/L, e.g. 1.2 mol/L, of the N,N-dialkylamide or mixture of N,N-dialkylamides.

As previously indicated, the aqueous solution used at step b) may comprise from 1 mol/L to 6 mol/L of nitric acid.

However, it is preferred that this aqueous solution should contain from 4 mol/L to 6 mol/L of nitric acid to facilitate the stripping of ruthenium and technetium from the organic solution resulting from step a). In this case, step b) advantageously also comprises a de-acidification of the organic solution, this de-acidification comprising at least one contacting of the organic solution with an aqueous solution comprising from 0.1 mol/L to 1 mol/L and better still 0.5 mol/L of nitric acid, followed by a separation of the organic and aqueous solutions.

According to the invention, the contacting of the organic and aqueous solutions in the extractor in which step $c_1$) takes place, comprises a circulation of these solutions in the extractor with an O/A flowrate ratio that is advantageously higher than 1, preferably equal to or higher than 3 and better still equal to or higher than 5 so as to obtain a concentrating stripping of plutonium, i.e. a plutonium stripping leading to an aqueous solution in which the concentration of plutonium is higher than the concentration of this element in the organic solution from which it is stripped.

The reducing agent(s) contained in the aqueous solution used at step $d_1$) is (are) preferably selected from among uranous nitrate (also called «U(IV)»), hydrazinium nitrate (also called «hydrazine nitrate»), hydroxylammonium nitrate (also called «hydroxylamine nitrate»), acetaldoxime and mixtures thereof such as a mixture of uranous nitrate and hydrazinium nitrate, a mixture of uranous nitrate and hydroxylammonium nitrate or a mixture of uranous nitrate and acetaldoxime, preference being given to a mixture of uranous nitrate and hydrazinium nitrate or a mixture of uranous nitrate and hydroxylammonium nitrate that is preferably used at a concentration ranging from 0.1 mol/L to 0.3 mol/L and typically of 0.2 mol/L.

In addition, step $d_1$), which can be performed at ambient temperature, is nevertheless preferably performed at a temperature ranging from 30 to 40° C. and better still at 32° C. to promote the kinetics of technetium stripping whilst best limiting phenomena of re-oxidation of this element in aqueous phase. The extractor in which step $d_1$) takes place is therefore preferably heated to a temperature of between 30° C. and 40° C.

According to the invention, step $d_2$) preferably further comprises an acidification of the aqueous solution resulting from step $d_1$), this acidification comprising an addition of nitric acid to the extractor in which step $d_2$) takes place to bring the concentration of nitric acid in the aqueous solution to a value of at least 2.5 mol/L.

Step e) can be conducted at ambient temperature. However, it is preferably conducted at a temperature ranging from 40° C. to 50° C., here again to promote the stripping of uranium. The extractor in which step e) takes place is therefore preferably heated to a temperature of between 40° C. and 50° C.

Irrespective of the temperature at which step e) is conducted, the contacting of the organic and aqueous solutions in the extractor in which this step takes place comprises a circulation of these solutions in this extractor with an O/A flowrate ratio higher than 1 so as to obtain a concentrating stripping of uranium, i.e. a uranium stripping leading to an aqueous solution in which the concentration of uranium is higher than the concentration of this element in the organic solution from which it is stripped.

As previously indicated, the method of the invention further comprises a step f) to regenerate the organic solution resulting from step e), this regeneration preferably comprising at least one washing of the organic solution with a basic aqueous solution, followed by at least one washing of the organic solution with an aqueous solution of nitric acid.

In addition to those already mentioned, the method of the invention also has the following advantages:
- the stripping of uranium is easier to implement than in the PUREX process since it can be conducted both at ambient temperature and under heat using an O/A flowrate ratio higher than 1, which allows a concentrating stripping of uranium which is not possible with the PUREX process;
- through the fact that it does not involve any reduction reaction of plutonium and thereby eliminates any risk of plutonium re-oxidation, the stripping of plutonium is also easier to implement than in the PUREX process and can be performed in more concentrating manner than in the latter process; these advantages carry all the more weight since the future processing plants of spent nuclear fuels will have to process fuels with higher plutonium content (eg. MOX fuels from light water or fast neutron reactors) than those currently being reprocessed;
- the degradation products (via hydrolysis and radiolysis) of the N,N-dialkylamides are less problemaic than those with TBP since they are water-soluble and do not form complexes likely to retain plutonium;
- the N,N-dialkylamides typically have a solubility in aqueous phase that is 100 to 200 times lower than that of TBP, which allows envisaging to omit or at least to reduce the number of washes with organic diluent of the aqueous solutions resulting from the method of the invention, compared with the number provided by the PUREX process;
- since the N,N-dialkylamides and their degradation products only comprise atoms of carbon, hydrogen, oxygen and nitrogen, they are fully incinerable and therefore do not produce penalizing secondary waste, unlike TBP and its degradation products.

Other characteristics and advantages of the invention will become apparent from the additional description given below.

However, this additional description is evidently solely given to illustrate the subject of the invention and is not under any circumstance to be construed as limiting this subject.

BRIEF DESCRIPTION OF THE FIGURE

FIG. 1 gives a flow diagram of the method of the invention for processing an aqueous nitric solution resulting from the dissolution of a spent nuclear fuel; in this FIGURE, the rectangles 1 to 7 represent multi-stage extractors such as those conventionally used for processing spent nuclear fuels (mixer-settlers, pulsed columns or centrifuge extractors); the organic phases are symbolized by solid lines whilst the aqueous phases are symbolized by dotted lines.

DETAILED DESCRIPTION OF PARTICULAR EMBODIMENTS

I—Synthesis of N,N-Dialkylamides of the Invention

As previously mentioned, the N,N-dialkylamides of the invention can be obtained with the following reaction scheme:

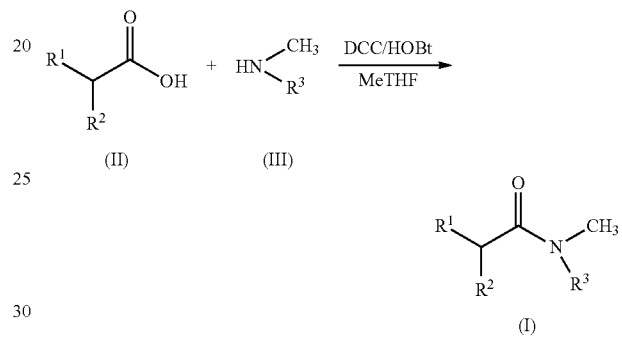

with $R^1=C_1-C_4$ linear alkyl group; $R^2=C_1-C_{10}$ linear alkyl group; and $R^3=C_6-C_{15}$ linear or branched alkyl group.

For this reaction, in a round bottom flask fitted with a septum and magnetic stir bar and under a nitrogen atmosphere, the DCC (1.2 eq.) and HOBt (1.2 eq.) are dissolved in 2-methyltetrahydrofurane (MeTHF) at 0.1 mol/L. Then, the carboxylic acid of formula (II) (1 eq.) is added and the reaction medium is left under agitation for 10 minutes at ambient temperature. The amine of formula (III) (1 eq.) is next added dropwise and the reaction medium left under agitation overnight at ambient temperature.

Thereafter, the reaction medium is filtered on Célite™. The filtrate is washed three times with an aqueous sodium carbonate-saturated solution ($Na_2CO_3$) and once with an aqueous sodium chloride-saturated solution (NaCl). The organic phase is collected, dried over anhydrous magnesium sulfate ($MgSO_4$), filtered and concentrated in a Rotavapor.

The reaction product is purified by silica column chromatography (elution with heptane/AcOEt: 100:0 at 75:25, v/v) and the N,N-dialkylamide of formula (I) is obtained in the form of two rotamers (colourless or pale yellow liquid, yield: from 60% to quantitative).

I.1—Synthesis of N-methyl-N-nonyl-2-methylhaxanamide or MNMHA

MNMHA, which meets above formula (I) wherein $R^1$ is a methyl group, $R^2$ is an n-butyl group whilst $R^3$ is an n-nonyl group, was synthesized as described above from 2-methylhexanoic acid and N-methyl-N-nonylamine. The characterizations thereof were the following:

TLC (silica gel): $R_f=0.33$ (heptane/AcOEt 8:2, v/v)
$^1$H NMR (400 MHz, $CDCl_3$) δ (ppm): 3.33 (m, 1H, $NCH_2$); 3.20 (m, 1H, $NCH_2$); 2.92 and 2.83 (2s, 3H, $NCH_3$, 2 rotamers); 2.56 (m, 1H, CH); 1.63-1.26 (m, 4H, 2 CH$_2$); 1.25-1.11 (m, 16H, 8 CH$_2$); 1.00 (m, 3H, CH$_3$); 0.79 (m, 6H, 2 CH$_3$)

$^{13}$C NMR (100 MHz, CDCl$_3$) δ (ppm): 176.7; 176.3; 49.8; 47.8; 35.7; 35.4; 35.2; 34.2; 33.9; 33.6; 31.8; 31.8; 29.8; 29.7; 29.5; 29.5; 29.4; 29.3; 29.2; 29.2; 28.9; 27.2; 26.8; 26.7; 22.8; 22.7; 22.6; 22.6; 18.0; 17.4; 14.0; 14.0; 13.9; 13.9

IR: ν=2956, 2924, 2855, 1641 (C=O), 1465 cm$^{-1}$

MS (ESI positive mode): m/z 270 [M+H]$^+$, 333 [M+ACN+Na]$^+$, 562 [2M+Na]$^+$

HRMS (EI positive mode): calculated for C$_{17}$H$_{35}$NO: 269.2719; found: 269.2723.

I.2—Synthesis of N-methyl-N-octyl-2-propylpentanamide or MOPPA

MOPPA, which meets formula (I) above where R$^1$ and R$^2$ are both an n-propyl group whilst R$^3$ is an n-octyl group, was synthesized from 2-propylpentanoic acid and N-methyl-N-octylamine. The characterizations thereof were the following:

TLC (silica gel): R$_f$=0.37 (heptane/AcOEt 8:2, v/v)

$^1$H NMR (400 MHz, CDCl$_3$) δ (ppm): 3.25 (t, J=7.5 Hz, 1H, NCH$_2$); 3.17 (t, J=7.6 Hz, 1H, NCH$_2$); 2.89 and 2.80 (2s, 3H, NCH$_3$, 2 rotamers); 2.50 (m, 1H, CH); 1.55-1.34 (m, 4H, 2 CH$_2$); 1.31-1.09 (m, 16H, 8 CH$_2$); 0.77-0.72 (m, 9H, 3 CH$_3$)

$^{13}$C NMR (100 MHz, CDCl$_3$) δ (ppm): 176.1; 175.8; 49.8; 47.8; 40.9; 40.7; 35.3; 35.3; 35.3; 33.5; 31.7; 31.6; 29.2; 29.2; 29.2; 29.1; 28.9; 27.2; 26.8; 26.7; 22.5; 22.5; 20.8; 20.7; 14.2; 14.1; 14.1; 13.9; 13.9.

IR: ν=2955, 2925, 2856, 1639 (C=O), 1464 cm$^{-1}$

MS (ESI positive mode): m/z 270 [M+H]$^+$, 333 [M+ACN+Na]$^+$, 562 [2M+Na]$^+$

HRMS (EI positive mode): calculated for C$_{17}$H$_{35}$NO: 269.2719; found: 269.2727.

I.3—Synthesis of N-methyl-N-hexyl-2-propylheptanamide or MHPHepA

MHPHepA, which meets above formula (I) where R$^1$ is an n-propyl group, R$^2$ is an n-pentyl group whilst R$^3$ is an n-hexyl group, was synthesized from 2-propylheptanoic acid and N-methyl-N-hexylamine. The characterizations thereof were the following:

TLC (silica gel): R$_f$=0.31 (heptane/AcOEt 8:2, v/v)

$^1$H NMR (400 MHz, CDCl$_3$) δ (ppm): 3.30 (dt, J=1.8 Hz, J=7.1 Hz, 1H, NCH$_2$); 3.21 (dt, J=2.2 Hz, J=6.9 Hz, 1H, NCH$_2$); 2.94 and 2.85 (2s, 3H, NCH$_3$, 2 rotamers); 2.53 (m, 1H, CH); 1.59-1.39 (m, 4H, 2 CH$_2$); 1.36-1.14 (m, 16H, 8 CH$_2$); 0.83-0.76 (m, 9H, 3 CH$_3$).

$^{13}$C NMR (100 MHz, CDCl$_3$) δ (ppm): 176.2; 176.0; 49.9; 47.9; 41.2; 41.0; 35.5; 35.4; 35.4; 33.7; 33.2; 33.1; 32.1; 32.0; 31.6; 31.5; 29.0; 27.5; 27.3; 27.2; 26.5; 26.5; 22.6; 22.5; 20.9; 20.8; 14.3; 14.2; 14.0; 14.0; 13.9.

IR: ν=2956, 2926, 2857, 1638 (C=O), 1459 cm$^{-1}$

MS (ESI positive mode): m/z 270 [M+H]$^+$, 333 [M+ACN+Na]$^+$

HRMS (EI positive mode): calculated for C$_{17}$H$_{35}$NO: 269.2719; found: 269.2732.

II—Extracting Properties of the N,N-Dialkylamides of the Invention

II.1—Acquisition of Uranium Distribution Coefficients

Extraction tests were conducted using:
- as organic phases: solutions comprising 0.4 mol/L of MNMHA or MOPPA or MHPHepA dans le TPH; and
- as aqueous phases: aqueous solutions comprising 12 g/L of uranium(VI) and either 4 mol/L of HNO$_3$ or 0.5 mol/L of HNO$_3$ (to simulate the aqueous phase of weak acidity which is typically used to strip plutonium at the U/Pu partitioning step into two aqueous streams).

Each of these tests was performed, in a tube and under agitation, by contacting one of the organic phases with one of the aqueous phases for 30 minutes at 25° C. The O/A volume ratio used was 1. These phases were separated from each other after centrifugation.

The concentrations of uranium were measured in the separated organic and aqueous phases by Inductively Coupled Plasma Atomic Emission Spectroscopy (ICP-AES).

II.2—Acquisition of Plutonium Distribution Coefficients

Extraction tests similar to those described under item 11.1 above were conducted but using, as aqueous phases, aqueous solutions which comprised 12 g/L of uranium(VI), 4 mol/L of HNO$_3$ or 0.5 mol/L of HNO$_3$, and plutonium(IV) (≈0.4 MBq/mL).

After separating the phases, the concentrations of uranium were measured in the organic and aqueous phases by ICP-AES, whilst the activities of $^{239+240}$plutonium were measured in the organic and aqueous phases by α-spectrometry.

II.3—Results

Table 1 below, for each tested N,N-dialkylamide, gives the distribution coefficients of uranium denoted D$_u$, and of plutonium denoted D$_{Pu}$, such as obtained with the aqueous phases at 4 mol/L of HNO$_3$ and at 0.5 mol/L d'HNO$_3$, and the U/Pu separation factors denoted FS$_{U/Pu}$ such as obtained with the aqueous phases at 0.5 mol/L of HNO$_3$.

This Table also gives the experimental results obtained under the same operating conditions but using, as organic phases, solutions comprising N,N-dialkylamides of the prior art, namely:

one solution comprising 0.32 mol/L of N,N-di(2-ethylhexyl)-isobutanamide (or DEHiBA) and 0.18 mol/L of N,N-di(2-ethylhexyl)-n-butanamide (or DEHBA) in TPH, these two N,N-dialkylamides being proposed in reference [3] under the names DOiBA and DOBA; and one solution comprising 0.5 mol/L of N,N-di(2-ethylhexyl)-3,3-dimethylbutanamide (or DEHDMBA) in TPH, this N,N-dialkylamide being proposed in reference [1] under the name DOTA.

TABLE I

| | | Organic phase | | | | |
|---|---|---|---|---|---|---|
| | | MNMHA 0.4M | MOPPA 0.4M | MHPHepA 0.4M | DEHiBA 0.32M + DEHBA 0.18M | DEHDMBA 0.5M |
| $HNO_3$ 4M | $D_U$ | 1.22 | 1.50 | 1.64 | 1.43 | 2.46 |
| | $D_{Pu}$ | 0.148 | 0.129 | 0.117 | 0.20 | 0.28 |
| $HNO_3$ 0.5M | $D_U$ | 0.026 | 0.030 | 0.035 | 0.030 | 0.025 |
| | $D_{Pu}$ | 0.0012 | 0.0023 | 0.0013 | 0.004 | 0.0015 |
| | $FS_{U/Pu}$ | 22 | 13 | 27 | 7 | 16 |

This Table shows that, when used at a concentration de 0.4 mol/L in organic phase, the N,N-dialkylamides of the invention extract uranium(VI) and plutonium(IV) from an aqueous nitric phase sufficiently well ($D_U$>1; $D_{Pu}$>0.1) to allow a quantitative co-extraction of uranium(VI) and plutonium(IV) in a method for processing an aqueous solution resulting from the dissolution of a spent nuclear fuel in nitric acid, in which they will be used at a concentration ranging from 1 mol/L to 2 mol/L.

An excellent U(VI)/Pu(IV) selectivity is reached with a nitric acid concentration of 0.5 mol/L ($FS_{U/Pu}$>12) with very low distribution coefficients of plutonium(IV) ($D_{Pu}$<0.0030). In particular, MHPHepA allows an $FS_{U/Pu}$ separation factor of 27 to be obtained.

Therefore, in a method for processing an aqueous solution resulting from the dissolution of a spent nuclear fuel in nitric acid in which the N,N-dialkylamides of the invention will be used at a concentration ranging from 1 mol/L to 2 mol/L, it will be possible to selectively strip plutonium(IV) from the organic phase resulting from the U(VI)/Pu(IV) co-extraction using an aqueous phase comprising 0.5 mol/L of nitric acid.

As also shown in Table 1, the N,N-alkylamides of the invention, with a nitric acid concentration of 0.5 mol/L, exhibit a U(VI)/Pu(IV) selectivity that is higher than that obtained with the DEHiBA/DEHBA mixture of reference [3], whilst having the advantage of being able to be used alone rather than in a mixture.

The performance of the N,N-alkylamides of the invention is close to that of DEHDMBA in reference [1]. However, they have the advantage of being less viscous than the latter (this being one of the limiting parameters for the development of a method with DEHDMBA for processing an aqueous solution resulting from the dissolution of a spent nuclear fuel in nitric acid) since the viscosity at 25° C. of an organic phase comprising 1.2 mol/L of MNMHA or MOPPA in TPH is 2.25 mPa/s and 2.16 mPa/s respectively, whilst it is 3.6 mPa/s for an organic phase comprising 1.27 mol/L of DEHDMBA in TPH.

III—Flowchart of the Method of the Invention for Processing an Aqueous Solution of a Dissolved Spent Nuclear Fuel Reference is made to FIG. 1 giving a flowchart of the method of the invention for processing an aqueous solution of a spent nuclear fuel dissolved in nitric acid.

As shown in this FIGURE, the method comprises 8 steps.

The first of these steps, denoted «U/Pu co-extraction» in FIG. 1, is intended to extract uranium and plutonium jointly, the first in oxidation state +VI and the second in oxidation state +IV, from the aqueous nitric solution of dissolved spent nuclear fuel.

Said solution typically comprises from 3 to 6 mol/L of $HNO_3$, uranium, plutonium, minor actinides (americium, curium and neptunium), fission products (La, Ce, Pr, Nd, Sm, Eu, Gd, Mo, Zr, Ru, Tc, Rh, Pd, Y, Cs, Ba, . . . ) and some corrosion products such as iron.

The «U/Pu co-extraction» step is performed by circulating the dissolution solution in extractor 1, in counter-current flow to an organic phase (denoted «OP» in FIG. 1) which comprises from 1 mol/L to 2 mol/L and better still from 1.1 mol/L to 1.4 mol/L, e.g. 1.2 mol/L, of an N,N-dialkylamide of the invention or of a mixture of N,N-dialkylamides of the invention in solution in an organic diluent.

This organic diluent is an aliphatic, linear or branched, hydrocarbon such as n-dodecane, TPH or the isoparaffinic diluent marketed by TOTAL under the trade name Isane IP 185T, preference being given to TPH.

The second step of the method, denoted «FP washing» in FIG. 1, is intended to strip, from the organic phase resulting from «U/Pu co-extraction», the fraction of fission products that was extracted from the dissolution solution jointly with uranium and plutonium.

This «FP washing» step comprises one or more washing operations of the organic phase resulting from «U/Pu co-extraction», each washing operation being conducted by circulating this organic phase in extractor 2, in counter-current flow to an aqueous nitric solution having a concentration possibly ranging from 1 mol/L to 6 mol/L of $HNO_3$, but preferably from 4 mol/L to 6 mol/L of $HNO_3$ and better still from 4 to 5 mol/L of $HNO_3$, to facilitate the stripping of ruthenium and technetium.

If the «FP washing» step is conducted with one or more strongly acidic aqueous solutions, i.e. typically of 3 mol/L d'$HNO_3$ or higher, then this step also comprises a de-acidification of the organic phase, which is performed by circulating this organic phase in counter-current flow to an aqueous nitric solution of low acidity, i.e. comprising from 0.1 mol/L to 1 mol/L of $HNO_3$ such as an aqueous solution comprising 0.5 mol/L of $HNO_3$, to prevent too much acid being carried into the extractor dedicated to the third step, denoted «Pu stripping» in FIG. 1, which would perturb the performance of this third step.

The «Pu stripping» step, which represents the first step of the U/Pu partitioning, is intended to strip plutonium in oxidation state +IV, hence without reducing this plutonium, from the organic phase resulting from «FP washing».

This step is performed by circulating this organic phase in extractor 3, in counter-current flow to an aqueous solution comprising from 0.1 mol/L to 0.5 mol/L of $HNO_3$ and preferably using an O/A flowrate ratio higher than 1, preferably of 3 or higher, and better still of 5, to obtain a concentrating stripping of plutonium(IV).

The stripping of plutonium(IV), which is performed at the «Pu stripping» step, is accompanied by a stripping of a fraction of the uranium(VI) which is also contained in the organic phase resulting from «FP washing».

Therefore, the fourth step of the method, denoted «1$^{st}$ U washing» in FIG. 1 and which represents the second step of the U/Pu partitioning, is intended to extract from the aqueous phase resulting from «Pu stripping»:

either the entirety of the uranium contained in this aqueous phase if it is desired that the U/Pu partitioning should lead to an aqueous solution comprising plutonium without uranium, and to an organic solution comprising uranium without plutonium;

or the amount of uranium with which it is possible, at the end of «1$^{st}$ U washing», to obtain an aqueous solution comprising uranium and plutonium in a previously chosen ratio, if it is desired that U/Pu partitioning should lead to an aqueous solution comprising a mixture of plutonium and uranium in this ratio, and to an organic solution comprising uranium without plutonium.

In both cases, the «1$^{st}$ U washing» is performed by circulating, in extractor 4, the aqueous phase resulting from «Pu stripping» in counter-current flow to an organic phase having the same composition as the organic phase used for «U/Pu co-extraction». The amount of uranium extracted is adjusted by acting both on the ratio of O/A flowrates and on the acidity of the aqueous phase, the extraction of uranium being bettered the higher the organic phase/aqueous phase flowrate ratio and the higher the acidity of the aqueous phase. An addition of HNO$_3$ of greater or lesser concentration to the aqueous phase circulating in extractor 4 can therefore be provided as a function of the acidity it is desired to impart to this aqueous phase.

The fifth step, denoted «α-Tc barrier» in FIG. 1, is intended to strip, from the organic phase resulting from «Pu stripping», the technetium fraction that was extracted at «U/Pu co-extraction» and not stripped at «FP washing», for the purpose of decontaminating this organic phase with respect to technetium.

It also allows stripping, from the organic phase resulting from «Pu stripping», the neptunium fraction that was extracted at «U/Pu co-extraction» and followed technetium up to «α-Tc barrier», as well as the traces of plutonium that this organic phase may still contain.

It is performed by circulating, in extractor 5, the organic phase resulting from «Pu stripping» in counter-current flow to an aqueous nitric solution of low acidity, i.e. comprising from 0.1 mol/L to 3 mol/L of HNO$_3$ and better still 1 mol/L of HNO$_3$, and comprising one or more reducing agents to reduce technetium—which is contained in the organic phase in oxidation state +VII—to technetium(IV) non-extractable by the N,N-dialkylamides, neptunium(VI) to neptunium(IV) or neptunium(V) which are non-extractable by the N,N-dialkylamides under weak acidity, and plutonium(IV) to plutonium(III) which is less extractable by the N,N-dialkylamides under weak acidity than plutonium(IV), whilst without reducing uranium(VI).

As reducing agents, uranous nitrate (or U(IV)), hydrazinium nitrate (or NH), hydroxylammonium nitrate (or NHA), acetaldoxime can be used, or a mixture thereof such as a U(IV)/NH, U(IV)/NHA or U(IV)/acetaldoxime mixture, preference being given to a U(IV)/NH or U(VI)/NHA mixture. Gluconic acid can be added to the aqueous solution to reduce phenomena of technetium re-oxidation in aqueous phase and thereby limit the consumption of reducing agent(s).

This step can be conducted at ambient temperature (i.e. 20-25° C.) but it is preferably conducted at a temperature ranging from 30° C. to 40° C. and better still at 32° C. to promote the stripping kinetics of technetium whilst limiting phenomena of technetium re-oxidation in aqueous phase and hence limit the risk that the technetium, once stripped, of being re-extracted in the organic phase.

The sixth step, denoted «2$^{nd}$ U washing» in FIG. 1, is intended to extract, from the aqueous phase resulting from «α-Tc barrier», the uranium that was back-extracted together with technetium at the preceding step, so that the «α-Tc barrier» step does not lead to a large loss of uranium in aqueous phase.

It is performed by circulating, in extractor 6, the aqueous phase resulting from «α-Tc barrier» in counter-current flow to an organic phase having the same composition as the organic phases used for «U/Pu co-extraction» and «1$^{st}$U washing», after an acidification of this aqueous phase with the addition of concentrated nitric acid, e.g. 10 M, to promote the extraction of uranium.

The seventh step, denoted «U stripping» in FIG. 1, is intended to strip uranium(VI) from the organic phase resulting from «α-Tc barrier».

It is performed by circulating, in extractor 7, the organic phase resulting from «α-Tc barrier» in counter-current flow to an aqueous nitric solution of very low acidity, i.e. comprising no more than 0.5 mol/L and better still no more than 0.05 mol/L of HNO$_3$, e.g. an aqueous solution comprising 0.01 mol/L of HNO$_3$. This step can be conducted at ambient temperature (i.e. at 20-25° C.) but is preferably conducted under heat (i.e. typically at a temperature of 40-50° C.) using an O/A flowrate ratio higher than 1 to obtain a concentrating stripping of uranium(VI).

After these 7 steps, the following are obtained:

two raffinates corresponding to the aqueous phases respectively leaving extractors 1 and 6, the first comprising fission products together with americium and curium («Primary raffinate» in FIG. 1), and the second comprising technetium, neptunium and optionally traces of plutonium («Secondary raffinate» in FIG. 1);

the aqueous phase leaving extractor 4, which comprises either decontaminated plutonium or a mixture of decontaminated plutonium and uranium, and called «Pu stream» or «Pu+U stream» accordingly;

the aqueous phase leaving extractor 7, which comprises decontaminated uranium, called «U stream»; and the organic phase leaving extractor 7, which no longer comprises either plutonium or uranium but may contain a certain number of impurities and degradation products of the extractant (formed by hydrolysis and radiolysis) which may have accumulated over the preceding steps.

Therefore, the eighth step, denoted «OP washing» in FIG. 1, is intended to regenerate this organic phase by subjecting it to one or more washes with an aqueous basic solution, e.g. a first wash with an aqueous 0.3 mol/L solution of sodium carbonate, followed by a second wash with an aqueous 0.1 mol/L solution of sodium hydroxide, then one or more washes with an aqueous nitric acid solution for re-acidification, e.g. an aqueous solution comprising 2 mol/L of HNO$_3$, each wash being performed by circulating said organic phase in an extractor, in counter-current flow to the aqueous wash solution.

As can be seen in FIG. 1, the organic phase thus regenerated can be returned to extractors 1 and 4 to be fed back into the processing cycle.

CITED REFERENCES

[1] FR-A-2 591 213
[2] FR-A-2 642 561

[3] FR-A-2 642 562
[4] Ruikar et al., *Journal of Radioanalytical and Nuclear Chemistry* 1993, 176(2), 103-111
[5] Prabhu et al., *Radiochimica Acta* 1993, 60, 109-114
[6] Cui et al., *Radiochimica Acta* 2005, 93, 287-290
[7] Sun et al., *Journal of Radioanalytical and Nuclear Chemistry* 2005, 264(3), 711-713

What is claimed is:

1. A method for separating totally or partially uranium (VI) from plutonium(IV) from an acid aqueous solution A1, comprising:
   a) a co-extraction of uranium and plutonium from the aqueous solution A1, the co-extraction comprising at least one contacting of the aqueous solution A1 with an organic solution S1 comprising an N,N-dialkylamide or a mixture of N,N-dialkylamides of formula (I):

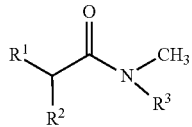

(I)

wherein:
   $R^1$ is a linear alkyl group having 1 to 4 carbon atoms;
   $R^2$ is a linear alkyl group having 1 to 10 carbon atoms;
   $R^3$ is a linear or branched alkyl group having 6 to 15 carbon atoms;
provided that $R^3$ differs from an n-octyl, n-decyl, n-dodecyl, 2-ethylhexyl and 2-ethyloctyl group when $R^1$ is an n-butyl and $R^2$ is an ethyl group; in an organic diluent, followed by a separation of the aqueous solution A1 from the organic solution S1;
   b) a stripping of plutonium, in oxidation state +IV, and of a fraction of uranium from the organic solution S1 resulting from a), the stripping comprising at least one contacting of the organic solution S1 with an aqueous solution A2 comprising from 0.1 mol/L to 0.5 mol/L of nitric acid, followed by a separation of the organic solution S1 from the aqueous solution A2; and
   c) an extraction of all or part of the uranium fraction contained in the aqueous solution A2 resulting from b), the extraction comprising at least one contacting of the aqueous solution A2 with an organic solution S2 identical to the organic solution S1 of a), followed by a separation of the aqueous solution A2 from the organic solution S2;
   whereby there are obtained an aqueous solution comprising plutonium without uranium, or a mixture of plutonium and uranium, and an organic solution comprising uranium without plutonium.

2. The method of claim 1, wherein the organic solution S1 of a) comprises from 1 mol/L to 2 mol/L of the N,N-dialkylamide or mixture of N,N-dialkylamides.

3. The method of claim 1, wherein the acid aqueous solution A1 is an aqueous solution resulting from a dissolution of a spent nuclear fuel in nitric acid.

4. The method of claim 1, wherein $R^1$ is a methyl, ethyl or n-propyl group.

5. The method of claim 1, wherein $R^2$ is an n-propyl, n-butyl, n-pentyl, n-hexyl or n-heptyl group.

6. The method of claim 1, wherein $R^3$ is an n-hexyl, n-heptyl, n-octyl, 2-ethylhexyl, n-nonyl, n-decyl or 2-ethyloctyl group.

7. The method of claim 1, wherein:
   $R^1$ is a methyl group, $R^2$ is an n-butyl group and $R^3$ is an n-nonyl group; or
   $R^1$ and $R^2$ are each an n-propyl group and $R^3$ is an n-octyl group; or
   $R^1$ is an n-propyl group, $R^2$ is an n-pentyl group and $R^3$ is an n-hexyl group.

8. A single-cycle method for processing an aqueous solution A1 resulting from a dissolution of a spent nuclear fuel in nitric acid, the aqueous solution A1 comprising uranium, plutonium, americium, curium and fission products including technetium, the cycle comprising:
   a) a co-extraction of uranium and plutonium from the aqueous solution A1, the co-extraction comprising at least one contacting, in an extractor, of the aqueous solution A1 with an organic solution S1 comprising an N,N-dialkylamide or a mixture of N,N-dialkylamides of formula (I):

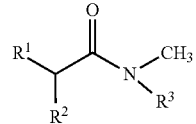

(I)

wherein:
   $R^1$ is a linear alkyl group having 1 to 4 carbon atoms;
   $R^2$ is a linear alkyl group having 1 to 10 carbon atoms;
   $R^3$ is a linear or branched alkyl group having 6 to 15 carbon atoms;
provided that $R^3$ differs from an n-octyl, n-decyl, n-dodecyl, 2-ethylhexyl and 2-ethyloctyl group when $R^1$ is an n-butyl and $R^2$ is an ethyl group; in an organic diluent, followed by a separation of the aqueous solution A1 from the organic solution S1;
   b) a decontamination of the organic solution S1 resulting from a) with respect to americium, curium and fission products, the decontamination comprising at least one contacting, in an extractor, of the organic solution S1 with an aqueous solution A2 comprising from 1 mol/L to 6 mol/L of nitric acid, followed by a separation of the organic solution S1 from the aqueous solution A2;
   c) a partitioning of the uranium and plutonium contained in the organic solution S1 resulting from b) into an aqueous solution comprising either plutonium without uranium, or a mixture of plutonium and uranium, and an organic solution comprising uranium without plutonium, the partitioning comprising:
      $c_1$) a stripping of plutonium, in oxidation state +IV, and of a fraction of uranium from the organic solution S1 resulting from b), the stripping comprising at least one contacting, in an extractor, of the organic solution S1 with an aqueous solution A3 comprising from 0.1 mol/L to 0.5 mol/L of nitric acid, followed by a separation of the organic solution S1 from the aqueous solution A3;
      $c_2$) an extraction of all or part of the uranium fraction contained in the aqueous solution A3 resulting from $c_1$), the extraction comprising at least one contacting, in an extractor, of the aqueous solution A3 with an organic solution S2 identical to the organic solution S1 of a), followed by a separation of the aqueous solution A3 from the organic solution S2;

d) a decontamination of the organic solution S2 resulting from $c_1$) with respect to technetium, the decontamination comprising:
  $d_1$) a stripping of technetium, in oxidation state +IV, from the organic solution S2 resulting from $c_1$), the stripping comprising at least one contacting, in an extractor, of the organic solution S2 with an aqueous solution A4 comprising from 0.1 mol/L to 3 mol/L of nitric acid and at least one reducing agent capable of reducing technetium from oxidation state +VII to oxidation state +IV, followed by a separation of the organic solution S2 from the aqueous solution A4;
  $d_2$) an extraction of the uranium fraction contained in the aqueous solution A4 resulting from $d_1$), the extraction comprising at least one contacting, in an extractor, of the aqueous solution A4 with an organic solution S3 identical to the organic solution S1 of a), followed by a separation of the aqueous solution A4 from the organic solution S3;
e) a stripping of the uranium from the organic solution S3 resulting from $d_1$), the stripping comprising at least one contacting, in an extractor, of the organic solution S3 with an aqueous solution A5 comprising no more than 0.5 mol/L of nitric acid, followed by a separation of the organic solution S3 from the aqueous solution A5; and
f) a regeneration of the organic solution S3 resulting from e);
whereby a first and a second aqueous solution are obtained, decontaminated with respect to americium, curium and fission products including technetium, the first aqueous solution comprising plutonium without uranium, or a mixture of plutonium and uranium, and the second aqueous solution comprising uranium without plutonium.

9. The method of claim 8, wherein the organic solution S1 of a) comprises from 1 mol/L to 2 mol/L of the N,N-dialkylamide or mixture of N,N-dialkylamides.

10. The method of claim 8, wherein the aqueous solution A2 of b) comprises from 4 mol/L to 6 mol/L of nitric acid.

11. The method of claim 8, wherein b) further comprises a de-acidification of the organic solution S1, the de-acidification comprising at least one contacting of the organic solution S1 with an aqueous solution A6 comprising from 0.1 mol/L to 1 mol/L of nitric acid, followed by a separation of the organic solution S1 from the aqueous solution A6.

12. The method of claim 8, wherein the contacting of the organic solution S1 and the aqueous solution A3 in the extractor of $c_1$) comprises a circulation of the organic solution S1 and the aqueous solution A3 in the extractor with a ratio of the organic solution S1 flowrate to the aqueous solution A3 flowrate higher than 1.

13. The method of claim 8, wherein $d_2$) comprises an acidification of the aqueous solution A4 resulting from $d_1$), to bring the concentration of nitric acid in the aqueous solution A4 to a value of at least 2.5 mol/L, the acidification comprising an addition of nitric acid to the extractor of $d_2$).

14. The method of claim 8, wherein the contacting of the organic solution S3 and the aqueous solution A5 in the extractor of e) comprises a circulation of the organic solution S3 and the aqueous solution A5 in the extractor with a ratio of the organic solution S3 flowrate to the aqueous solution A5 flowrate higher than 1.

15. The method of claim 8, wherein the aqueous solution A1 is an aqueous solution resulting from a dissolution of a spent nuclear fuel in nitric acid.

16. The method of claim 8, wherein $R^1$ is a methyl, ethyl or n-propyl group.

17. The method of claim 8, wherein $R^2$ is an n-propyl, n-butyl, n-pentyl, n-hexyl or n-heptyl group.

18. The method of claim 8, wherein $R^3$ is an n-hexyl, n-heptyl, n-octyl, 2-ethylhexyl, n-nonyl, n-decyl or 2-ethyloctyl group.

19. The method of claim 8, wherein:
  $R^1$ is a methyl group, $R^2$ is an n-butyl group and $R^3$ is an n-nonyl group; or
  $R^1$ and $R^2$ are each an n-propyl group and $R^3$ is an n-octyl group; or
  $R^1$ is an n-propyl group, $R^2$ is an n-pentyl group and $R^3$ is an n-hexyl group.

* * * * *